(12) United States Patent
Prenzel et al.

(10) Patent No.: US 7,678,041 B2
(45) Date of Patent: Mar. 16, 2010

(54) AIRPLANE SEAT, PASSENGER BENCH, MAGNETIC FIELD RESONANCE SYSTEM, AND USE OF A DEVICE FOR GENERATING ELECTROMAGNETIC INTERACTION IN AN AIRPLANE SEAT OR IN A PASSENGER BENCH IN AN AIRCRAFT

(75) Inventors: Eric Prenzel, Jork (DE); Johannes Schmeelk, Hammah (DE)

(73) Assignee: Airbus Deutschland GmbH (DE)

( * ) Notice: Subject to any disclaimer, the term of this patent is extended or adjusted under 35 U.S.C. 154(b) by 588 days.

(21) Appl. No.: 11/294,291

(22) Filed: Dec. 5, 2005

(65) Prior Publication Data

US 2006/0145457 A1    Jul. 6, 2006

Related U.S. Application Data

(60) Provisional application No. 60/633,460, filed on Dec. 6, 2004.

(30) Foreign Application Priority Data

Dec. 6, 2004    (DE) .................. 10 2004 058 722

(51) Int. Cl.
*A61N 2/00* (2006.01)
(52) U.S. Cl. ............................................. 600/9
(58) Field of Classification Search .............. 600/9–15; 297/217.3, 180.12, 284.1; 601/57
See application file for complete search history.

(56) References Cited

U.S. PATENT DOCUMENTS

| | | | |
|---|---|---|---|
| 5,930,152 A * | 7/1999 | Dumont et al. ............. | 700/302 |
| 6,682,494 B1 * | 1/2004 | Sleichter et al. ............ | 601/57 |
| 6,776,753 B1 * | 8/2004 | Holcomb .................... | 600/15 |
| 7,326,170 B1 * | 2/2008 | Miller ........................ | 600/9 |

FOREIGN PATENT DOCUMENTS

| | | |
|---|---|---|
| CA | 2 513 610 | 8/2004 |
| CA | 2 514 985 | 8/2004 |
| DE | 200 05 453 U1 | 6/2000 |
| DE | 101 09 429 A1 | 9/2002 |
| DE | 101 41 673 A1 | 3/2003 |
| DE | 102 16 009 A1 | 10/2003 |
| DE | 103 01 867 A1 | 7/2004 |
| DE | 103 02 439 A1 | 7/2004 |
| DE | 103 04 085 A1 | 8/2004 |
| DE | 103 04 093 A1 | 8/2004 |
| GB | 2295093 A * | 5/1996 |

* cited by examiner

*Primary Examiner*—Charles A Marmor, II
*Assistant Examiner*—Christine D Hopkins
(74) *Attorney, Agent, or Firm*—Lerner, David, Littenberg, Krumholz & Mentlik, LLP

(57) ABSTRACT

A seat with a device for generating electromagnetic interaction in an accommodation region that is equipped to accommodate an object. By electromagnetic interaction, an object can be influenced in such a way that, for example, fatigue that occurs during long-distance flights can be avoided. The device is used to prevent and reduce the occurrence of jet lag, reduce the danger of passengers suffering from thrombosis, and increase general well-being by promoting relaxation, sleep and stress reduction. The integration in cabin crew seats and/or cockpit seats can improve the performance of the crew of an aircraft on long-distance flights.

24 Claims, 4 Drawing Sheets

AIRPLANE SEAT, PASSENGER BENCH, MAGNETIC FIELD RESONANCE SYSTEM, AND USE OF A DEVICE FOR GENERATING ELECTROMAGNETIC INTERACTION IN AN AIRPLANE SEAT OR IN A PASSENGER BENCH IN AN AIRCRAFT

CROSS-REFERENCE TO RELATED APPLICATIONS

This application claims the benefit of the filing date of U.S. Provisional Patent Application No. 60/633,460 filed Dec. 6, 2004, the disclosure of which is hereby incorporated herein by reference.

BACKGROUND OF THE INVENTION

The present invention relates to an airplane seat, a passenger bench for an aircraft, a magnetic field resonance system, and a use of a device for generating electromagnetic interaction in an airplane seat or in a passenger bench for an aircraft.

Long-distance flights, long journeys in passenger motor vehicles or coaches in confined spaces entail an uncomfortable seating position for passengers. Apart from the passengers, members of the crew are also affected. Remaining in the same seated position, combined with limited opportunities to move around, in many cases leads to the danger of suffering from thrombosis. Moreover, long journeys can entail changes in time zones. If such journeys are made in confined spaces, the body can experience stress situations, and manifestations can be experienced which, for passengers and aircrew alike, can lead to the phenomenon known as jet lag.

DE 103 04 085 A1, DE 103 04 093 A1, DE 103 02 439 A1 and DE 103 01 867 A1 disclose devices which are based on the principle of electromagnetic resonance stimulation (eMRS). One example of this is the eMRS® system of the company vita-life®.

vita-life® eMRS® can for example be used as supplementary treatment:
for regenerative function—bone system;
for regenerative function—soft tissue;
as a relaxation function—vegetative soothing;
for improved provision of oxygen;
as a function that stimulates circulation;
as a pain-relieving function—bony joint system; and
as a pain relieving function—connective tissue.

The function of the devices is based on the effect which electromagnetic and magnetic fields have on living organisms.

First there was the empirical knowledge of old cultures with the positive effect of magnets on health and beauty. After a considerable period when this was forgotten and after a brief reawakening of the interest in medieval times and at the beginning of the modern age, magnetic-field research made its breakthrough by recognising the pathogenesis as a result of a lack of electromagnetic information. There followed a phase of euphoric, uncritical and undifferentiated use: in cosmetics, in the wellness sphere, and in conjunction with other fashion trends. This boom caused considerable damage to serious magnetic field research. The latter has increasingly been classified as frivolous and thus not to be taken seriously.

Irrespective of these western fashion trends, however, above all in Europe intensive high-level research has continued without interruption. In the early 21st century, as part of information medicine and energy medicine, there has again been an increased focus on the therapeutic options of electromagnetic waves, and, in the context of environmental medicine and the problematic nature of electrosmog, this research discipline attains a dimension of urgency.

SUMMARY OF THE INVENTION

According to an embodiment of the present invention, an airplane seat is disclosed which comprises an accommodation region and a device for generating electromagnetic interaction. This device for generating electromagnetic interaction is designed such that it generates electromagnetic interaction in the accommodation region. In this arrangement the accommodation region is designed to accommodate an object, and the device for generating electromagnetic interaction is accommodated in the seat, in particular integrated in the seat.

This may allow to prevent stress situations for humans.

Furthermore, the invention provides for a bench that comprises a plural number of seats with the characteristics described above, wherein the seats are arranged side by side.

Moreover, according to the invention a means of transport is provided, comprising a seat or comprising a bench with the characteristics described above.

In addition, the invention states a magnetic-field resonance system that is designed for operation in an aircraft. The term "magnetic-field resonance system" refers in particular to a device by means of which magnetic-resonance therapy can be carried out, i.e. by means of which humans can be treated in a targeted way using electromagnetic fields.

Also, the invention discloses the use of a device for generating electromagnetic interaction in a seat or in a bench.

Electromagnetic interaction is one of the four basic forces of nature; the others being gravitation, week interaction and strong interaction. Electricity and magnetism are manifestations of electromagnetic interaction. Electromagnetic interaction describes the influence which purely electric, purely magnetic or electromagnetic fields have on objects and spatial characteristics.

A device for generating electromagnetic interaction in the accommodation region can result in electromagnetic interaction with an object, situated in the accommodation region, taking place. For example, the object can sit or lie in the accommodation region while the electromagnetic interaction has an effect on the object. Advantageously, on a seat with an integrated device for generating electromagnetic interaction, electromagnetic interaction can thus take place so as to be directed to the seated object (for example a human being or an animal). Such electromagnetic interaction has a positive effect on the object, triggered by the interaction of material of the object with an electric and/or magnetic field. In this way stress situations in the object can be reduced, or they can be prevented from arising in the first place—wherein such stress situations can in particular occur during a journey, which stress situations a person can for example suffer in a means of locomotion—when seated on the seat according to the invention.

Electromagnetic interaction can be regarded as the basis of all life. The physiology of the turn of the millennium is on the brink of a revolution in the biological sciences. The fundamental significance electromagnetic forces have on living systems is becoming increasingly clear. Seeing the organism as a self-regulating complex system with its own communication options and control options leads to an ever more profound understanding of life, and to completely new approaches to therapy. Life is characterised by metabolism, growth and propagation.

The metabolism is controlled by way of electromagnetic processes: for example, by way of electrical potentials on the cell membrane, ions are also "pumped" against concentration gradients (active metabolism). The body's water management and electrolyte management is partly based on phenomena which are connected to electromagnetic interaction. Communication with the outside world, information transmission, the function and coordination of inner organs and muscular contractions, including those of the myocardium (ECG) take place by electrical stimulation (NS). Likewise, the brain's increased nerve activity and ability to function is based on bioelectricity (EEG). In an object, for example in the human body, magnetic fields as particular instances of electromagnetic interaction can cause changes that are similar to those that arise during exercise, and can thus support normal biological processes. Biological effectiveness of a generated alternating magnetic or electromagnetic field can arise as a result of:

- electromagnetic influence the field has on the ion currents in an object, for example a human body (for example sodium-potassium pumps, Ca-cascade);
- magnetomechanical influence the magnetic field has on the oscillation amplitude of cells and organs (resonance);
- ionic-cyclotronic resonance of anions and cations of the bodily fluids of an object to strengthen the intrinsic rotational momentum (spin);
- nuclear magnetic resonance (NMR); and
- electron spin resonance (ESR).

Advantageously, electromagnetic interaction can give rise to biophysiological effects. The term "biophysiological effects" refers in particular to the bioelectrical effect, the biochemical effect and the bioenergetic effect.

The bioelectrical effect can for example cause normalisation of a cell membrane. In pathological cases the potential can drop as a result of the ingress of positive ions, for example of Na+, into the interior of the cell. In order to reverse this process, the cell requires energy which it can obtain from ATP hydrolysis.

The biochemical effect is based on an increase in enzyme activity, as well as on activation of the oxidation-reductive processes that are connected with ATP. In this, the Ca++ that has been produced from the Ca-cascade is the effective ion.

The bioenergetic effect is a factor that stimulates nutrition and cell growth. Furthermore, this effect controls intracellular processes that lead to regeneration of the body.

In many various ways over the past years the effectiveness of pulsating electromagnetic field therapy has been proven and made visible.

- By means of dark-field microscopy the resolution of pseudohaemagglutination (rouleaux formation) of erythrocytes can be proven. This leads to improvements in blood viscosity, improvements in blood-flow characteristics, enlargement of the surface, increased oxygen content, and reduced danger of thrombosis.
- Bone density measurements make it possible to detect a significant increase in bone density after treatment over an extended period of time.
- Infrared thermography measuring provides proof of improved blood circulation.
- Measuring the skin conductance potential at acupuncture-meridian end points (PROGNOS method) documents regulation of body energy.
- Combined biofeedback measuring shows optimisation of a multitude of body functions after just a few minutes of applying pulsating magnetic fields.
- Photoplethysmography measurements show improvements in blood circulation averaging in excess of 45% in the region of microcirculation, and an increase in oxygen saturation in the blood averaging 25%.

By means of the invention, stimulation of melatonin production and stabilisation of the waking-sleeping rhythm, in particular during a journey, may be brought about, during which a human being is seated on the seat according to the invention. This can advantageously counteract an energy deficit or jet lag. An object, in particular a human being, passenger or member of the crew of an aircraft or some other means of transport or means of locomotion (for example a passenger motor vehicle, lorry, coach, ship etc.) can thus arrive from a long journey in a relaxed state and without fatigue. Thus, according to one embodiment the invention implements a magnetic resonance system in a seat so that already during a journey actively impending stress situations that would otherwise lead to jet lag and similar phenomena are counteracted. Implementing a device for generating electromagnetic interaction (i.e. an electromagnetic force) in a seat thus provides a particularly favourable field of application for such a device, because in this way real-time causes of a stress-situation can be countered.

Likewise, an improvement in the oxygen supply and nutrient supply as well as in the blood circulation can take place. As a result of this improved oxygen supply in the tissue, in this way the thrombosis danger can be reduced in a way that is similar to performance optimisation that can be carried out in top-class sports by means of electromagnetic interaction.

Through this effect during seated activities, for example during a flight, the health, well-being and performance of passengers, pilots and cabin crew can be maintained and improved through the use of electromagnetic resonance stimulation (eMRS). In this way, treatment after a journey, in particular after a flight, can be avoided. For example an MRS system is stated in DE 103 04 085 A1.

Improved blood circulation and oxygen uptake in passengers should result in the danger of circulatory disturbances and thromboses being reduced. By integrating a device for generating electromagnetic interaction in a seat, in particular in the case of aircraft, seats for various applications can be produced. It should be weighed up whether seats according to the invention are to be used for a particular group of passengers, for example first-class passengers or business-class passengers, or only as seats for the crew.

By using a device for generating electromagnetic interaction, in particular a magnetic-field resonance system, and furthermore in particular an electromagnetic resonance stimulation system (eMRS), electromagnetic interaction in an accommodation region for accommodating an object, of a seat or a bench, can be generated.

Preferred improvements of the invention are disclosed in the dependent claims.

According to exemplary embodiments of the invention, an airplane seat is stated in which the device for generating electromagnetic interaction is integrated in various elements of the seat. The device for generating electromagnetic interaction can be integrated in the seat surface, the backrest or the footrest, or in any desired combination of these three components of the seat.

Advantageously, integration of the device for generating electromagnetic interaction in elements of the seat makes it possible for the device not to be visible outside the seat and for said device to be accommodated in a space-saving manner, which is of importance in particular in means of transport such as a passenger aircraft. To a user of the seat, the seat is no different to look at than a known seat. For example, an object, i.e. for example a passenger, can be in the accommodation region of the seat.

As a rule, different body regions of a passenger are located in the region of the various seat elements. For example, the legs of a passenger tend to be on the seat element footrest, while the posterior region and the back region respectively of a passenger tend to be near the seat surface and the backrest respectively. In this way the effect of electromagnetic interaction on various body regions of the passenger can be matched in a controlled and targeted manner to physiological requirements.

Furthermore, the use of magnetic mats or one or several coils to generate electromagnetic interaction becomes possible. The device for generating electromagnetic interaction can be a coil or a magnetic mat. Often a magnetic mat comprises a coil whose form is matched to the mat. This coil or magnetic mat can be controlled by a control device.

According to a further exemplary embodiment of the present invention, the airplane seat comprises a user interface which is designed for user-defined adjustment of the electromagnetic interaction. Advantageously, by means of a user interface (for example some kind of remote control) a user is put in a position to make individual adjustments to the electromagnetic interaction. Users can thus match the effect to their individual requirements. For example, adjustment of the strength of an electric, a magnetic, or an electromagnetic field that acts on the user, in particular a passenger, can be made.

Advantageously, a user interface that is provided for setting the parameters of electromagnetic interaction could be integrated in an already existing control terminal or entertainment system. A user interface could also comprise a device for accommodating a chip card, on which a program code with instructions for the various settings is stored, and could load this code to the control unit from where it can be executed. Exchangeable chip cards provide an advantage in that at any time new characteristics and improvements of the system can be used, and in that the functionality can be optimally matched to a user (for example to body dimensions, gender, known illnesses, etc.). For example, a chip card could be provided specifically for a wellness program. A device for generating electromagnetic interaction with a wellness program would have the objective of creating a particular situation of well-being for the user. A further example relates to a chip card with a fitness program, which preferably could for example ensure improved blood circulation.

According to a further embodiment of the present invention, the seat comprises a sensor device which is designed to acquire a physiological parameter of an object arranged in the accommodation region. By means of the physiological parameter obtained, the device for generating electromagnetic interaction can be controllable. A sensor device could for example be a biofeedback sensor to determine the body state, at the time, of a user of the seat. The signals that are obtained from the body of the user can be transmitted to the seat, in particular to a control unit. This control unit can adjust the electromagnetic interaction (for example an electric, magnetic, or electromagnetic field strength) according to the state of the body of the object. Examples of measured values which could be used as biofeedback signals include skin resistance measuring, an electromyogramme (EMG), the temperature of the skin, an electroencephalogramme (EEG), oxygen-particle pressure measuring, or heart rate variability (HRV).

Biofeedback relates in particular to the feedback of measured data to the patient in order to influence his/her involuntary or unconscious bodily functions. Feedback of measured data need not necessarily be to the patient, but instead can be to therapy devices which as a result of the information obtained in this way can automatically adjust the course and dose of therapy in such a manner as to achieve maximum effect.

By means of biofeedback components, automatic control of the treatment procedure can take place. A finger sensor with which the heart rate variability (HRV) is continually measured is one example of a biofeedback sensor or a sensor device. The measured data cause real-time adjustment of the dosage, for example of an electric, magnetic or electromagnetic field. HRV as an energetic diagnostic method can be of interest because it measures a parameter which provides information on the entire organism of an object, rather than just providing a momentary snapshot at a specific point.

The finger sensor can be connected to the finger of an object or of a seated user and provides feedback that can be used for determining the dosage.

Advantageously the use of a sensor device makes it possible, in an effective and user-specific manner, to adjust electromagnetic interaction.

According to a further exemplary embodiment of the present invention, a display unit for the seat is stated. The display unit can be designed such that it can provide a colour spectrum to an object arranged in the accommodation region.

The provision of a colour spectrum, in particular of a colour spectrum that progressively changes in a determined temporal sequence, can assist in providing relaxation to objects, such as for example human beings. For example, a pair of colour-light spectacles can generate any desired colour of the entire colour spectrum from the primary colours red, green and blue. The three primary colours can be superimposed behind a diffuser screen such that a desired colour is generated. This desired colour can for example act on an open eye of the user. This can lead to a relaxed state of the user, which state can amplify the use of a concurrently acting electromagnetic interaction. This can for example in an aircraft prevent a passenger or a member of the crew from becoming fatigued. Further examples of a colour light component can include a monitor, a liquid crystal display or spectacles comprising a device for generating a colour spectrum. For example a display unit is stated in DE 103 01 867 A1.

According to a further exemplary embodiment of the present invention, a seat which comprises an acoustic playback unit is stated. The acoustic playback unit can be designed such that a frequency spectrum can be provided for an object that is arranged in the accommodation region. By means of the acoustic playback unit, for example a sound component, in particular headphones or a loudspeaker, frequencies can be provided to a user, which frequencies can amplify the effect of electromagnetic interaction, for example of a magnetic field, an electric field or an electromagnetic field. The display unit and the playback unit can also form part of an entertainment system that is for example present as standard equipment in passenger seats in an aircraft. A control device can handle coordination between acoustic signals for the sound components and can also handle the optical signals for the colour-light spectacles depending on the electromagnetic interaction.

The frequencies provided can for example be designed to generate music, vibrations or ultrasound.

The electromagnetic interaction can be a magnetic, electric or electromagnetic field. This field can be static, homogeneous or pulsating with a pulse form that can be predetermined in a targeted way. The pulse form can be from the group of a triangular form, a rectangular form and a sawtooth form. The term "sawtooth form" in particular refers to a multiple sawtooth pulse form which represents an overlay of a multitude of sawtooth forms. The frequency or the magnetic flux density can be varied in order to achieve certain effects. Practical experience has shown that pulsating magnetic-field systems can be even more advantageous than static magnets. Pulsating electromagnetic resonance systems with maximum flux densities of applicator-radiation of 1 to 500 µT, preferably 200-400 µT, can be therapeutically sensible. Integrating a magnetic-field resonance system in a passenger seat, cabin crew seat or cockpit seat can contribute to a reduction in jet lag and in a reduction in the danger of thrombosis, and increase the general well-being by promoting relaxation, sleep and stress reduction.

For example, a system for generating a homogeneous magnetic field is stated in DE 103 04 093 A1.

For magnetic-field therapy, preferably so-called extremely low frequency electromagnetic fields (ELF-EMF) are used, whose electrical parameters are smaller than, or equal to, those of the terrestrial magnetic field, while the intensity of its magnetic field is larger than, or equal to, that of the terrestrial magnet.

External magnetic fields have an effect on the charged particles that are present in biological systems. Said magnetic fields can deflect said particles (Lorentz force, Hall effect) and focus their radiation.

Magnetic fields with a frequency of 16 Hz have an influence on the cell membrane permeability of Ca-ions (cyclotron resonance). Apart from having such an influence on the ion flow, magnetic fields can also have an influence on paramagnetic particles, for example in coenzymes or prosthetic groups (for example the iron centre in the haemal plane of haemoglobin or myoglobin) and thus can have an influence on enzyme activity. They have an effect on liquid crystals and thus have an influence on membrane structures.

As a consequence of these biophysical mechanisms, various influences on metabolic activities occur. This includes effects on oxygen absorption of haemoglobin and cytochrome, tissue repair mechanisms and wound healing, osteogenesis, cardiovascular system and metabolic processes in nerve tissue and thus also in the central nervous system, as well as vasodilative, antiphlogistic and analgesic effects.

From this action spectrum, potential options of use arise in a large number of indications, for example pain syndromes, chronic inflammation, disorders of the locomotor apparatus, in particular in conjunction with osteogenesis, as well as ischaemia and circulatory disturbances, metabolic disorders, vegetative dysfunction and states of anergia.

In a positive manner the positive effects, in particular on circulatory disturbances and states of anergia, can contribute to the electromagnetic interaction contributing to a reduction in the danger of jet lag as well as to a reduction in the danger of thrombosis and an increase in the general well-being of a passenger or member of the crew of a means of transport.

According to a further exemplary embodiment of the present invention, a seat is stated which is constructed as a passenger seat. Advantageously the accommodation region of such a passenger seat can accommodate a passenger to be transported. It is thus possible to provide a transport service while simultaneously a positive influence as a result of electromagnetic interaction with the passenger or the member of the crew takes place. A passenger seat according to the present invention can be used in various means of conveyance, locomotion or transport, such as for example an aircraft, coach, tram, train or ship.

According to a further embodiment of the present invention, a bench is stated that comprises a plural number of seats which are arranged one beside the other. Providing a bench with several individual seats provided one beside the other makes it possible, for example, to install seats in an aircraft more effectively. In one attachment operation a plural number of seats that are arranged one beside the other can be installed, for example in an installation rail in the floor of an aircraft. This can accelerate the installation process during production of an aircraft. A device for generating electromagnetic interaction can be provided that is shared by all or by a part of the seats of a bench, which results in considerable cost advantages.

According to a further embodiment of the present invention, a magnetic-field resonance system for operation in an aircraft is disclosed. The use of a magnetic-field resonance system in an aircraft can require adaptation to the framework conditions that exist in an aircraft. It may be necessary, for example, to produce magnetic-field resonance systems which are adapted to the voltage, frequency or special connections (plug, socket) common in aircraft. These requirements can be different from requirements in other fields of application, for example domestic situations. It might for example also be necessary for the connections to be adapted to a current-rail system that is normally used in aircraft.

BRIEF DESCRIPTION OF THE DRAWINGS

Below, embodiments of the present invention are described in detail with reference to the following figures.

DETAILED DESCRIPTION

Figure 1:
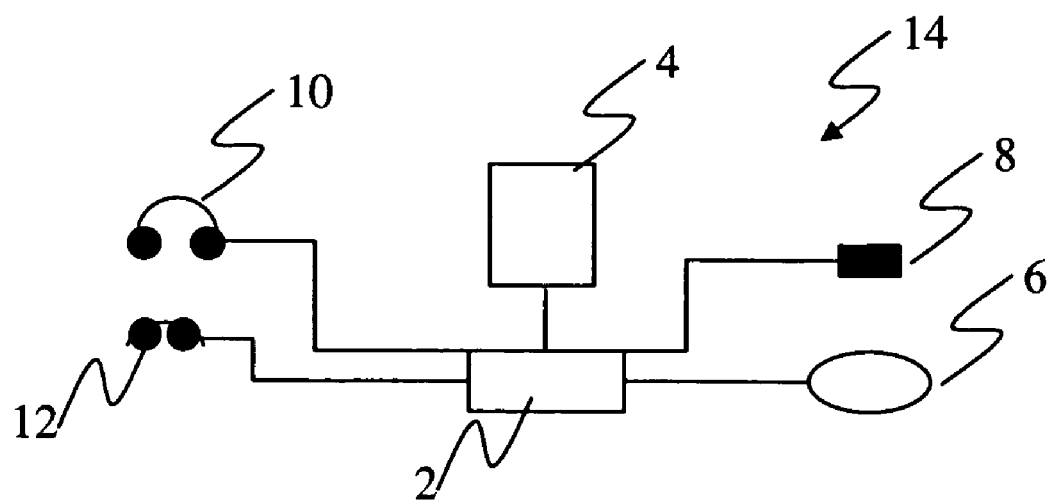
FIG. 1 shows a functional diagram of a device for regulating electromagnetic interaction, according to one embodiment of the invention.

The illustration in the figures are diagrammatic and are not to scale.

Identical or similar components in different figures have the same reference characters.

FIG. 1 shows a functional diagram of a device for regulating electromagnetic interaction. The central control device 2 determines inputs of the user interface 4 and of the sensor device 8. The data obtained by way of the user interface 4 or the sensor device 8 is processed in the control or regulating device 2 and is converted to signals for the acoustic playback unit 10, the display unit 12 and the device 6 for generating electromagnetic interaction. Depending on the parameters set on the user interface 4, for example, the flux density of a magnetic or electromagnetic field is set. In addition, biofeedback parameters that have been determined by means of the sensor device 8 can be used to set the field strength of the magnetic or electromagnetic field.

Control by means of biofeedback data by way of the sensor device 8 can take place in real time. This means that essentially at the same moment at which a change in the biofeedback data that is measured by the sensor device 8 takes place, after taking into account any computing time, adaptation of the electromagnetic interaction takes place by means of the device 6 for generating electromagnetic interaction. It is thus possible to react directly to changes in the state of the user.

For example heart rate variability (HRV), i.e. the variance in the heart beats or fluctuations in the heart rhythm that are determined by means of a finger sensor, can be used as a biofeedback signal. By means of the user interface 4 it is also possible, if so desired by a passenger or member of the crew, to select a program, for example a wellness program or a fitness program. In order to promote sleep or to reduce stress in the user, in addition acoustic signals can be made available by means of the acoustic playback unit 10 or optical signals can be provided by means of the display unit 12. The acoustic signals can be relaxation-promoting frequency spectra, music or ultrasound, while the optical signals are for example displayed on the colour-light spectacles 12 or on a liquid crystal display 12. In this arrangement the optical display unit 12 provides any colours from the entire colour spectrum, which colours are generated from the primary colours red, green and blue. These colours can have a direct effect on the open eyes of a user wearing the spectacles 12. Connection of the following components: user interface 4, device 6 for generating electromagnetic interaction, sensor device 8, acoustic playback unit 10 and display unit 12 to the control unit can be by cable or by wireless technology, for example radio waves or Bluetooth.

If required, the control console 4 can be removable and can be integrated in a passenger seat, for example a front passenger seat. The entire device for regulating electromagnetic interaction 14 comprising the control device 2, the user interface 4, the sensor device 8, the device 6 for generating electromagnetic interaction, the acoustic playback unit 10 and the display unit 12 can be accommodated in a passenger seat so that at least the components—control device 2 and device 6 for generating electromagnetic interaction—are not visible. Coupling the acoustic playback unit 10 for example with an entertainment system that is present as standard in an aircraft is possible. For each unit an additional weight of approximately 3 kg or less is to be calculated.

Figure 2:
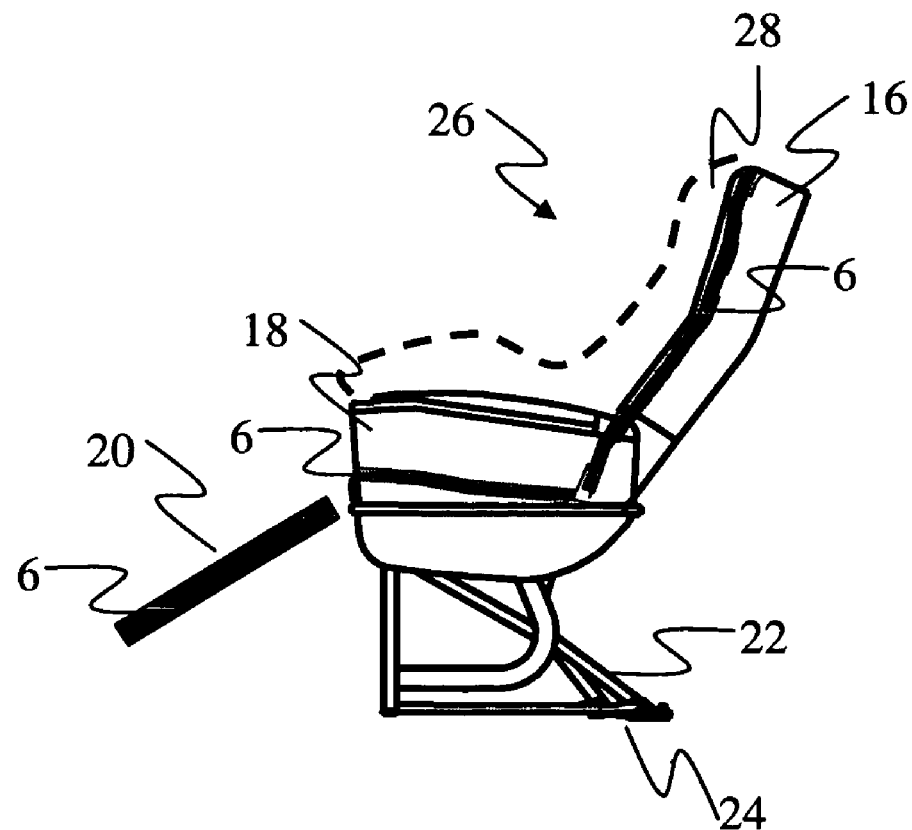
FIG. 2 shows a lateral section view of a seat with a device for generating electromagnetic interaction, according to an exemplary embodiment of the invention.

FIG. 2 shows a lateral section view of a seat 26 with a device 6 for generating electromagnetic interaction. The seat 26 comprises a seat frame 22 by means of which the seat is attached to the seat rail 24 in the floor, for example of an aircraft. The seat 26 comprises a backrest 16, a seat surface 18 and a footrest 20. Integrated in the backrest 16, the seat surface 18 and the footrest 20 is a device 6 for generating electromagnetic interaction. This can for example be a coil or several coils. The coil can be designed in single-coil technology or as a magnetic-field mat.

In a design as a magnetic-field mat 6 a single coil extends in the mat 6 in a spiral pattern according to a complex mathematical model. This coil emits an even and homogeneous magnetic field that is independent of the stature and weight of a passenger. The design as a single coil that is arranged in a mat-shape makes it possible to inconspicuously integrate the device 6 for generating electromagnetic interaction in the backrest 16, in the seat surface 18 or in the footrest 20. By determining the size of the region which is backed by the coil 6, the region of the electromagnetic interaction that acts on the passenger can be determined. In FIG. 2 the coil mat has been integrated in the backrest 16, the seat surface 18, and the footrest 20. In other words, a passenger or a member of the crew seated in the seat 26 can receive whole-body treatment.

When seated, a passenger or member of the crew or some other user of the seat is accommodated by the accommodation region 28. Due to the modular design of the device for regulating electromagnetic interaction 14 it is possible to retrofit said device to conventional passenger seats.

Depending on the requirement of the respective passengers, all the seats in an aircraft, or, for example, only seats of higher price categories such as first-class or business-class, can be equipped with the device for regulating electromagnetic interaction. When fitting out the seats of members of the crew, for example the cockpit crew or the cabin crew, the safety and well-being of the crew, for example of a pilot, is paramount. During a long-distance flight a pilot can use the seat 26 in order to recuperate better and faster, which improves flight safety.

However, it is also possible for particular regions of an aircraft, for example wellness regions, to be fitted with chairs 14 or seats 14. If need be, these chairs 14 or seats 14 can be used by individual passengers, i.e. they can be used for a fee.

Figure 3:
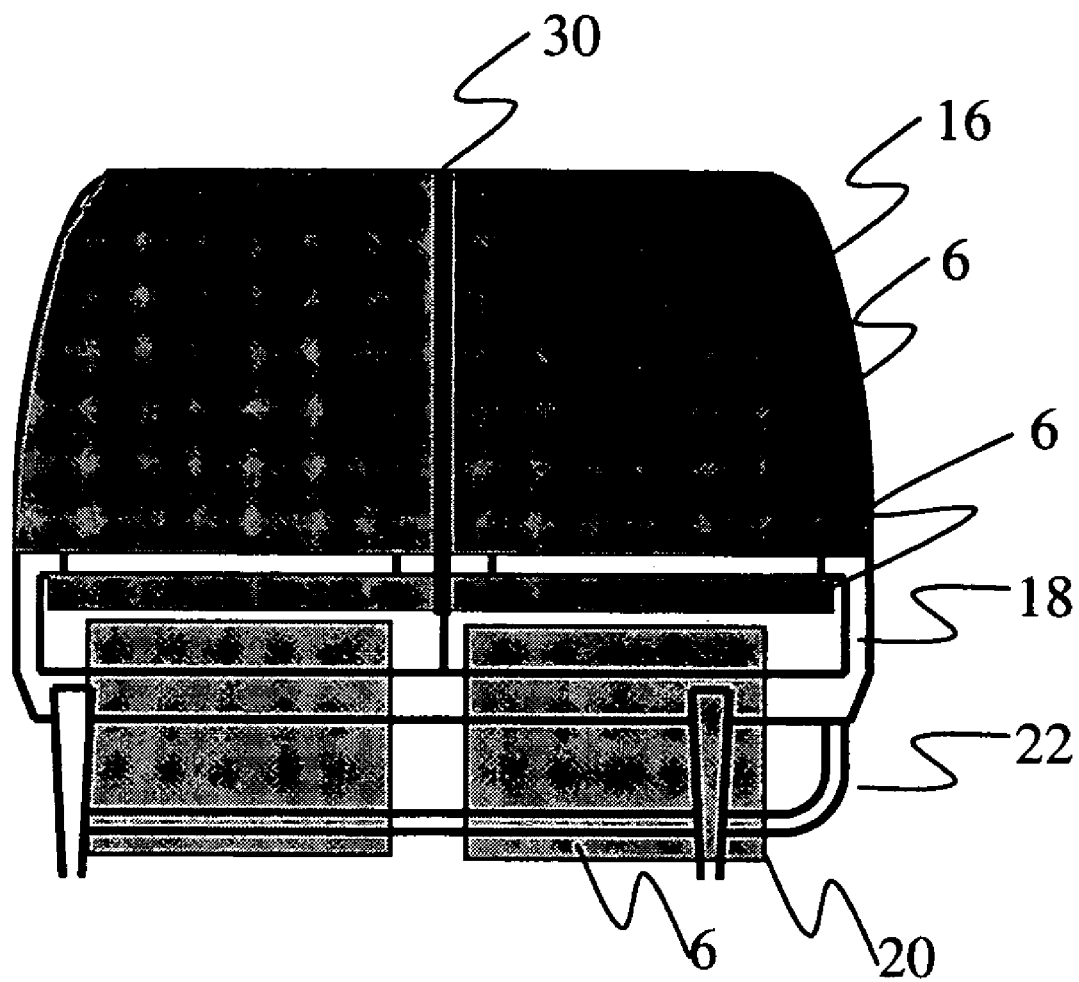
FIG. 3 shows a diagrammatic rear view of a seat with a device for generating electromagnetic interaction, according to an exemplary embodiment of the invention.

FIG. 3 shows a diagrammatic rear view of a seat with a device for generating electromagnetic interaction. The image shows a two-seat arrangement according to the present invention. The two seats of the seat arrangement shown are symmetrical in relation to the connection element 30. For this reason, only one seat is described below. Corresponding statements apply to the symmetrically arranged seat. The device 6 for generating electromagnetic interaction, for example a magnetic-field mat in single-coil technology, is integrated in the backrest 16, the seat surface 18 and the footrest 20. In FIG. 3 the backrest 16, the seat surface 18 and the footrest 20 have a magnetic-field mat of their own.

However, for easier installation and to achieve cost advantages it is also possible to use an individual mat which extends without interruption inside the backrest 16, the seat surface 18 and the footrest 20. The magnetic-field mats 6 are controlled by a control device 2 (not shown in FIG. 3). The backrest 16, the seat surface 18 and the footrest 20 of the two seats are arranged on the shared seat frame 22. Therefore, during installation it is not necessary to install two individual seats, but instead only a common seat arrangement. In this way the installation process can be accelerated.

Figure 4:
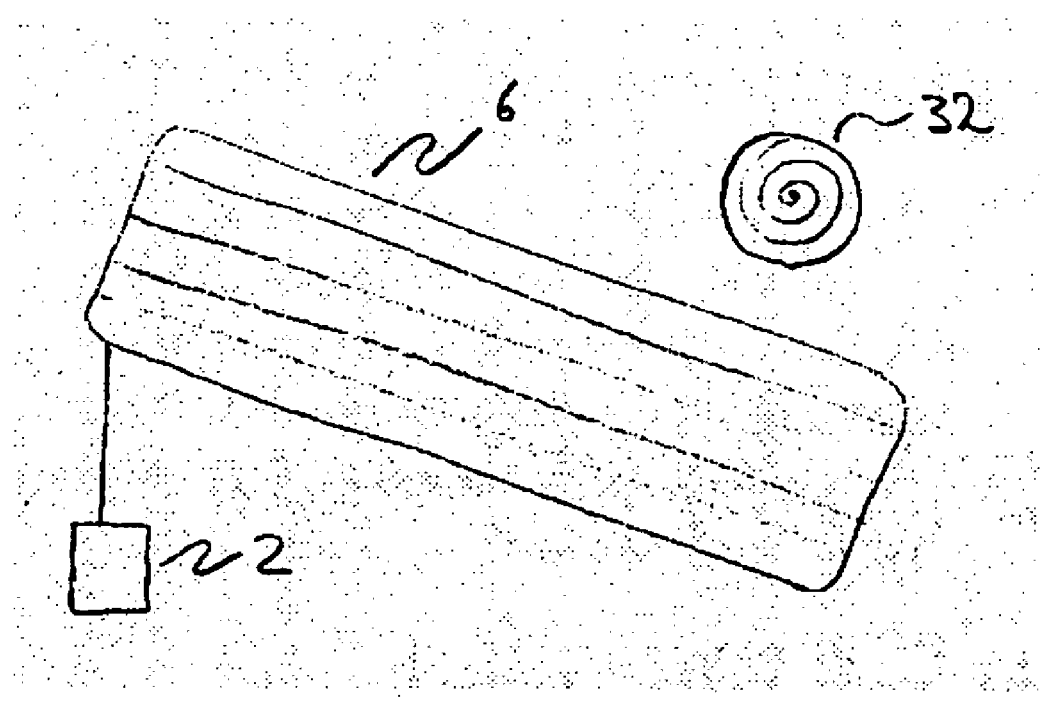
FIG. 4 shows a device for generating electromagnetic interaction, according to an exemplary embodiment of the invention.

FIG. 4 shows a device for generating electromagnetic interaction. The figure shows the magnetic-field mat 6, which due to the single-coil technology used is flexible, easy to handle and rollable. This single-coil technology essentially achieves the homogeneity (evenness) of one coil.

FIG. 4 shows the magnetic mat 6 both in the rolled-out and in the rolled-in 32 form. The magnetic mat is connected to the control device 2 which controls and adapts to the requirements of a passenger the magnetic flux density or magnetic field strength generated by the coil of the magnetic mat 6. Due to the flexibility of the magnetic mat 6 and its easy handling, the magnetic mat 6 can be produced in any desired size so that retrofitting it to already existing seats is facilitated. It is thus easily possible to retrofit the device to seats in trains, automobiles, aircraft, ships, coaches or trams, or other means of transport.

Figure 5:
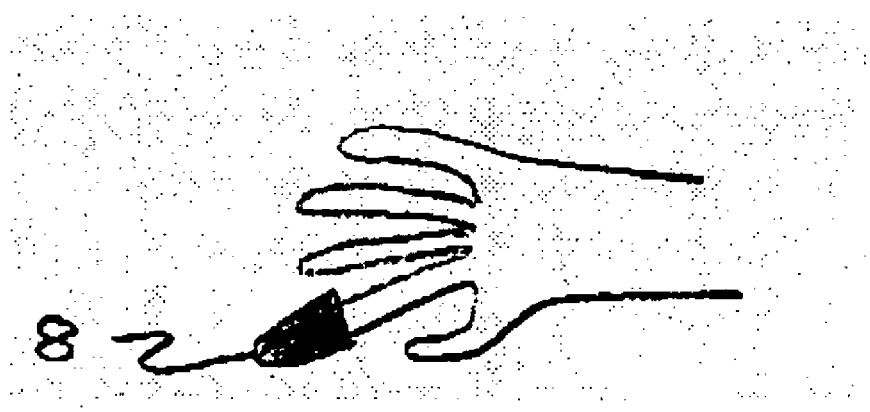
FIG. 5 shows a sensor device according to an exemplary embodiment of the invention.

FIG. 5 shows an embodiment of a sensor device. In FIG. 5 the embodiment of a sensor device as a finger clip 8 is shown. The finger clip 8 measures, on a finger of a hand, for example deviations of the heart rhythm. As a result of this, biofeedback signals are generated, which are conveyed to the control device 2. Based on these biofeedback signals, the control device 2 determines whether any increase or decrease in the treatment parameters, for example in the flux density or field strength of a coil, are necessary. This calculation can take place in real time. The biofeedback signal, for example the heart rhythm, is a measure that indicates the state of the patient and thus serves to control the therapy.

Possible treatment parameters are for example the pulse frequency of a pulsating electromagnetic field (ELF) or the signal form of said pulse frequency. Likewise, the necessary treatment duration can be determined. Typical values are: induction fields with flux densities ranging from 8 to 15 mT with a frequency of 10, 15 or 20 Hz with rectangular, triangular or sawtooth pulse or semi-triangular pulses for a duration of preferably 12 minutes, in particular 8-16 minutes.

Figure 6:
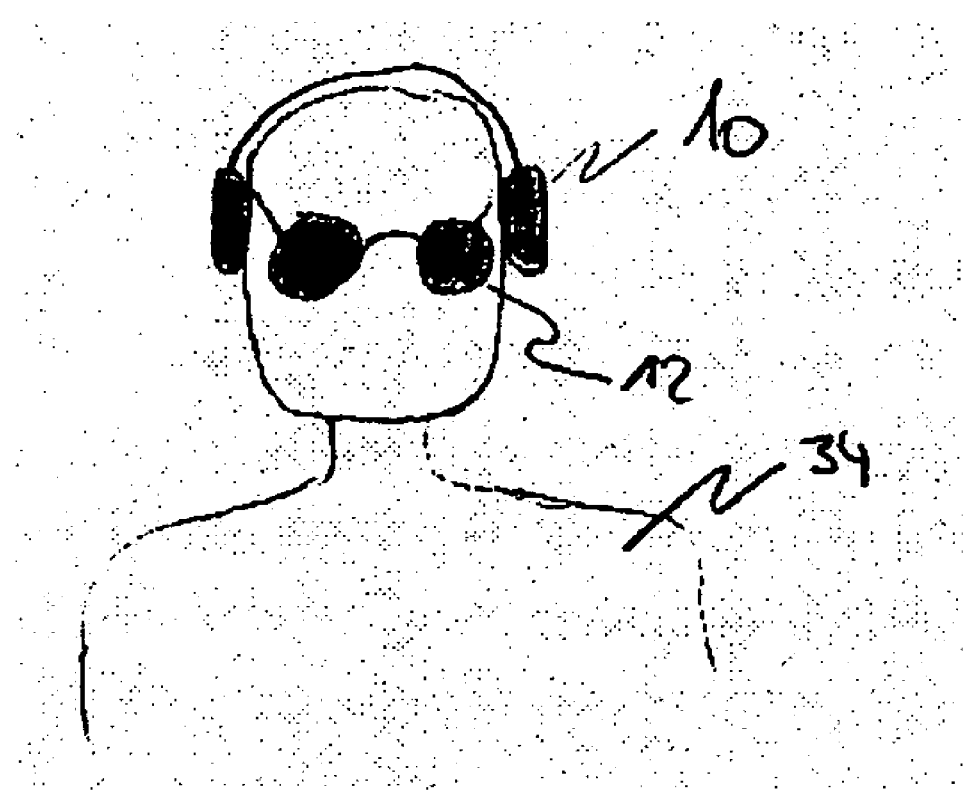
FIG. 6 shows a passenger with an acoustic playback unit and a display unit according to an exemplary embodiment of the invention.

FIG. 6 shows a passenger with an acoustic playback unit and a display unit. The display unit 12 is placed on the head of the passenger 34 in such a way that the colour spectra generated by the display unit 12 can have a direct effect on the open eyes. At the same time, by way of the acoustic playback unit, acoustic signals act on the passenger 34, wherein the frequencies of said acoustic signals are matched to the magnetic fields and the light spectrum. In this arrangement the acoustic playback unit 10 is pulled over the head of the passenger in such a way that the frequencies generated by the sound component 10 can have an effect on the ears of the user 34. The use of the optical display unit and of the acoustic playback unit 10 promotes the relaxation of the user, passenger or member of the crew during treatment with the magnetic field.

In addition it should be pointed out that "comprising" does not exclude other elements or steps, and "a" or "one" does not exclude a plural number. Furthermore, it should be pointed out that characteristics or steps which have been described with reference to one of the above embodiments can also be used in combination with other characteristics or steps of other embodiments described above. Reference characters in the claims are not to be interpreted as limitations.

The invention claimed is:

1. An airplane seat comprising:
an accommodation region;
an interaction device for generating electromagnetic interaction in the accommodation region;
a user interface and a sensor; and
an acoustic playback unit;
wherein the accommodation region is equipped for accommodating an object;
wherein the interaction device for generating electromagnetic interaction is accommodated in the airplane seat; and
wherein the user interface is connected to the interaction device for adjusting the electromagnetic interaction and wherein the sensor is arranged to acquire a physiological parameter of an object arranged in the accommodation region; and
wherein the acoustic playback unit is arranged to provide an acoustic frequency spectrum to an object arranged in the accommodation region.

2. The airplane seat of claim 1,
wherein the airplane seat further comprises an airplane seat surface;
wherein the interaction device for generating electromagnetic interaction is integrated in the airplane seat surface.

3. The airplane seat of claim 1,
wherein the airplane seat further comprises a backrest;
wherein the interaction device for generating electromagnetic interaction is integrated in the backrest.

4. The airplane seat of claim 1,
wherein the airplane seat comprises a footrest;
wherein the interaction device for generating electromagnetic interaction is integrated in the footrest.

5. The airplane seat of claim 1,
wherein the interaction device for generating electromagnetic interaction is controllable by the sensor device.

6. The airplane seat of claim 1,
wherein the interaction device for generating electromagnetic interaction generates a magnetic field in the accommodation region.

7. The airplane seat of claim 1,
wherein the interaction device for generating electromagnetic interaction generates an electromagnetic field in the accommodation region.

8. The airplane seat of claim 1,
wherein the interaction device for generating electromagnetic interaction generates a static electromagnetic interaction in the accommodation region.

9. The airplane seat of claim 8,
wherein the interaction device for generating electromagnetic interaction generates electromagnetic interaction that is essentially homogeneous in the accommodation region.

10. The airplane seat of claim 1,
wherein the interaction device for generating electromagnetic interaction generates pulsating electromagnetic interaction in the accommodation region.

11. The airplane seat of claim 10,
wherein the pulsating electromagnetic interaction comprises at least one pulse form from the group consisting of a triangular form, a rectangular form and a sawtooth form.

12. The airplane seat of claim 10,
wherein the pulsating electromagnetic interaction has a frequency ranging from 10 Hz to 20 Hz in the accommodation region.

13. The airplane seat of claim 6,
wherein the interaction device for generating electromagnetic interaction generates a magnetic flux density of a maximum of 100 mT in the accommodation region.

14. The airplane seat of claim 6,
wherein the interaction device for generating electromagnetic interaction generates a magnetic flux density of a maximum of 8 mT to 15 mT in the accommodation region.

15. The airplane seat of claim 6,
wherein the interaction device for generating electromagnetic interaction generates a magnetic flux density of 1 µT to 500 µT in the accommodation region.

16. The airplane seat of claim 1,
wherein the airplane seat is a passenger seat for a passenger aircraft.

17. An airplane passenger bench, comprising:
a plurality of airplane seats each comprising an accommodation region; and
an interaction device for generating electromagnetic interaction in the accommodation region; and
a user interface and a sensor; and
an acoustic playback unit;
wherein the accommodation region is equipped for accommodating an object;
wherein the interaction device for generating electromagnetic interaction is accommodated in the airplane seat;
wherein the plurality of airplane seats are arranged side by side;
wherein the user interface is connected to the interaction device for adjusting the electromagnetic interaction and wherein the sensor is arranged to acquire a physiological parameter of an object arranged in the accommodation region; and
wherein the acoustic playback unit is arranged to provide an acoustic frequency spectrum to an object arranged to the accommodation region.

18. A magnetic-field resonance system, for-operation in an aircraft having an accommodation region, the magnetic-field resonance system comprising:

an interaction device, the interaction device generating electromagnetic interaction in the accommodation region;
a user interface associated with the interaction device;
a sensor arranged to acquire a physiological parameter of an object arranged in the accommodation region; and
an acoustic playback unit;
wherein electromagnetic interaction is adjusted by the interaction device based on readings from the sensor or inputs from the user interface; and
wherein the acoustic playback unit is arranged to provide an acoustic frequency spectrum to an object arranged in the accommodation region.

19. A method for generating electromagnetic interaction in the region of one or both of an airplane seat or in an airplane passenger bench, the method comprising:
accommodating an object in the airplane seat or airplane passenger bench;
generating an electromagnetic interaction in the region of the airplane seat or airplane passenger bench;
acquiring a physiological parameter of the object accommodated in the airplane seat or airplane passenger bench;
adjusting the electromagnetic interaction based on the acquired physiological parameter or input from the object; and
providing an acoustic frequency spectrum acoustic by a playback unit to an object arranged in the accommodation region.

20. The method of claim 19,
wherein the generating of electromagnetic interaction is performed by use of a magnetic-field resonance system.

21. An airplane seat comprising:
an accommodation region;
an interaction device for generating electromagnetic interaction in the accommodation region;
a user interface and a sensor; and
a display unit;
wherein the accommodation region is equipped for accommodating an object;
wherein the interaction device for generating electromagnetic interaction is accommodated in the airplane seat; and
wherein the user interface is connected to the interaction device for adjusting the electromagnetic interaction and wherein the sensor is arranged to acquire a physiological parameter of an object arranged in the accommodation region; and
wherein the display unit is arranged to provide a colour spectrum to an object arranged in the accommodation region.

22. An airplane passenger bench, comprising:
a plurality of airplane seats each comprising an accommodation region; and
an interaction device for generating electromagnetic interaction in the accommodation region; and
a user interface and a sensor; and
a display unit;
wherein the accommodation region is equipped for accommodating an object;
wherein the interaction device for generating electromagnetic interaction is accommodated in the airplane seat;
wherein the plurality of airplane seats are arranged side by side;
wherein the user interface is connected to the interaction device for adjusting the electromagnetic interaction and wherein the sensor is arranged to acquire a physiological parameter of an object arranged in the accommodation region; and
wherein the display unit is arranged to provide a colour spectrum to an object arranged in the accommodation region.

23. A magnetic-field resonance system, for-operation in an aircraft having an accommodation region, the magnetic-field resonance system comprising:
an interaction device, the interaction device generating electromagnetic interaction in the accommodation region;
a user interface associated with the interaction device;
a sensor arranged to acquire a physiological parameter of an object arranged in the accommodation region; and
a display unit;
wherein electromagnetic interaction is adjusted by the interaction device based on readings from the sensor or inputs from the user interface; and
wherein the display unit is arranged to provide a colour spectrum to an object arranged in the accommodation region.

24. A method for generating electromagnetic interaction in the region of one or both of an airplane seat or in an airplane passenger bench, the method comprising:
accommodating an object in the airplane seat or airplane passenger bench;
generating an electromagnetic interaction in the region of the airplane seat or airplane passenger bench;
acquiring a physiological parameter of the object accommodated in the airplane seat or airplane passenger bench;
adjusting the electromagnetic interaction based on the acquired physiological parameter or input from the object; and
providing a colour spectrum on a display unit to an object arranged in the accommodation region.

* * * * *